United States Patent [19]

Clemence et al.

[11] Patent Number: 5,424,314
[45] Date of Patent: Jun. 13, 1995

[54] 20,21-DINOREBURNAMENINES

[75] Inventors: François Clemence, Paris; Jean-Luc Haesslein, Courtry; Claude Oberlander, Paris, all of France

[73] Assignee: Roussel-Uclaf, France

[21] Appl. No.: 207,361

[22] Filed: Mar. 7, 1994

Related U.S. Application Data

[63] Continuation of Ser. No. 941,677, Sep. 8, 1992, abandoned, which is a continuation of Ser. No. 655,725, Feb. 14, 1991, abandoned.

[30] Foreign Application Priority Data

Feb. 15, 1990 [FR] France ................... 90 01823

[51] Int. Cl.⁶ .................. A61K 31/445; C07D 461/00
[52] U.S. Cl. ........................ 514/283; 546/51
[58] Field of Search ............... 546/51; 514/283

[56] References Cited

U.S. PATENT DOCUMENTS 4,382,936 5/1983 Katsube et al. .............. 514/283
5,093,337 3/1992 Aktogu et al. .............. 514/283

FOREIGN PATENT DOCUMENTS 317427 5/1989 European Pat. Off. .

OTHER PUBLICATIONS

Aktogu, Chemical Abstract 112:56385c (1989).

*Primary Examiner*—Mukund J. Shah
*Attorney, Agent, or Firm*—Bierman and Muserlian

[57] ABSTRACT

A compound in all racemic or optionally active forms selected from the group consisting of a compound of the formula

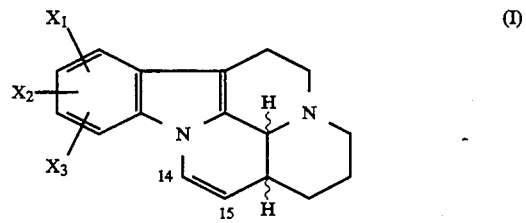

where the substituents are defined as in the specification and their non-toxic, pharmaceutically acceptable acid addition salts having anti-anoxic activity and a novel process and intermediates for their preparation.

7 Claims, No Drawings

20,21-DINOREBURNAMENINES

PRIOR APPLICATION

This application is a continuation of U.S. patent application Ser. No. 941,677 filed Sep. 8, 1992 now abandoned, which is a continuation of U.S. patent application Ser. No. 655,725 filed Feb. 14, 1991, now abandoned.

OBJECT OF THE INVENTION

It is an object of the invention to provide the novel 20,21-dinoreburnamenines of formula I and their non-toxic, pharmaceutically acceptable acid addition salts and a novel process and novel intermediates for their preparation.

It is another object of the invention to provide novel antianoxic compositions and a novel method of inducing antianoxic activity in warm-blooded animals.

These and other objects and advantages of the invention will become obvious from the following detailed description.

THE INVENTION

The novel compounds of the invention are 20,21-dinoreburnamenines in all racemic or optionally active forms selected from the group consisting of a compound of the formula

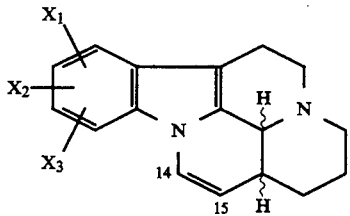

wherein $X_1$, $X_2$ and $X_3$ are individually selected from the group consisting of hydrogen, halogen, —OH, —NO$_2$, —CF$_3$, optionally substituted alkyl and alkoxy of 1 to 18 carbon atoms, optionally substituted alkenyl and alkynyl of 2 to 18 carbon atoms, —CN, acyl of an organic carboxylic acid of 1 to 8 carbon atoms, esterified carboxy, optionally substituted carbamoyl, alkylthio and haloalkylthio of 1 to 18 carbon atoms,

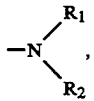

optionally substituted aryl of 6 to 10 carbon atoms, optionally substituted heteromonocyclic aryl of 5 to 6 ring members and optionally substituted condensed heterocyclic aryl, $R_1$ and $R_2$ are individually selected from the group consisting of hydrogen, optionally substituted alkyl of 1 to 7 carbon atoms, optionally substituted alkenyl of 2 to 7 carbon atoms, acyl of an alkanoic acid of 1 to 7 carbon atoms, benzoyl, optionally substituted carbocyclic or heterocyclic of 3 to 8 carbon atoms or $R_1$ and $R_2$ together with the nitrogen to which they are attached form an optionally unsaturated and optionally substituted heterocyclic of 5 to 6 ring members optionally containing a heteroatom selected from the group consisting of oxygen, sulfur and nitrogen and their non-toxic, pharmaceutically acceptable acid addition salts thereof, with the proviso that $X_1$, $X_2$ and $X_3$ are not simultaneously selected from the group consisting of hydrogen, halogen, alkyl and alkoxy of 1 to 5 carbon atoms, —OH, —CF$_3$, -nitro, —NH$_2$, mono and dialkylamino of 1 to 5 alkyl carbon atoms and acyl amino in which acyl is acyl of an aliphatic carboxylic acid of 1 to 6 carbon atoms and their non-toxic, pharmaceutically acceptable acid addition salts.

In the compounds of formula I, the 3-hydrogen and the 16-hydrogen can have α- or β-orientation which determines the existence of cis and trans diastereoisomers.

In the products of formula I, the term halogen is preferably chloride, but it can also be fluorine, bromine or iodine and linear or branched alkyl includes preferably lower alkyl such as methyl, ethyl, propyl or isopropyl, but can also be butyl isobutyl, sec-butyl, tert-butyl, pentyl or heptyl. Linear or branched alkoxy includes preferably methoxy or ethoxy but can also be propoxy, isopropoxy, linear, secondary or tertiary butoxy. Linear or branched alkenyl includes preferably vinyl, allyl, 1-propenyl, butenyl or pentenyl and linear or branched alkynyl includes preferably ethynyl, propargyl, butynyl or pentynyl. The alkyl, alkyloxy, alkenyl and alkynyl have preferably at most 8 carbon atoms.

Acyl of 1 to 8 carbon atoms includes preferably formyl, acetyl, propionyl, butyryl or benzoyl, but also a valeroyl, hexanoyl, acryloyl, crotonoyl or carbamoyl and esterified carboxy includes preferably lower alkoxy or aralkoxy carbonyl such as methoxycarbonyl, ethoxycarbonyl or benzyloxycarbonyl. Substituted carbamoyl includes N-(lower monoalkyl) carbamoyl such as N-methylcarbamoyl, N-ethylcarbamoyl; an N,N-(lower dialkyl) carbamoyl such as N,N-dimethylcarbamoyl, N,N-diethylcarbamoyl; an N-(lower hydroxyalkyl) carbamoyl such as N-(hydroxymethyl) carbamoyl, N-(hydroxyethyl) carbamoyl.

Alkylthio includes methylthio or ethylthio and haloalkylthio includes alkylthio substituted by at least one halogen such as fluoromethylthio, fluoroethylthio, chloroethylthio, dichloromethylthio, trifluoromethylthio or trifluoroethylthio. The alkylthio and haloalkylthio preferably have 1 to 4 carbon atoms.

—N($R_1$)($R_2$) can include mono- or dialkyl-, -alkenyl- or -alkynyl- amino in which the alkyl, alkenyl and alkynyl have the above meanings. The optionally substituted, saturated or unsaturated heterocyclic or carbocyclic that can be contained by —N($R_1$)($R_2$) can include non-aromatic or an aromatic group or an aryl. Examples of non-aromatics includes cycloalkyl, cycloalkenyl, cycloalkadienyl such as cyclohexyl, cyclopentyl, cyclobutyl, cyclopropyl, cyclohexadienyl such as 1,4-cyclohexadienyl, 1,3-dimethylcyclohexenyl, 1-cyclohexenyl.

Aryl includes carbocyclic or heterocyclic either condensed heteromonocyclic or condensed heterocyclic optionally substituted. Examples of optionally substituted aryl are the phenyl, naphth-1-yl; indenyl; saturated or unsaturated heterocyclic with 5, 6 or 7 links containing at least one heteroatom chosen from sulfur, nitrogen and oxygen. It is understood that when the heterocyclic has more than one heteroatom, the heteroatoms may be identical or different such as thien-2-yl and thien-3-yl, furyl such as fur-2-yl, pyridyl such as pyrid-2-yl, pyrimidyl, pyrrolyl, N-substituted pyrrolyl such as N-methylpyrrolyl, thiazolyl, isothiazolyl, diazolyl, triazolyl, tetrazolyl, thiadiazolyl, thiatriazolyl, oxazolyl, oxadiazolyl, 3- or 4-isoxazolyl, substituted 3- or 4-isoxazolyl such as 3-aryl-5-methylisoxazol-4-yl, the aryl being phenyl or halophenyl; condensed heterocyclic groups containing at least one heteroatom chosen from sulfur, nitrogen and oxygen such as benzothienyl like benzothien-3-yl, benzofuryl, benzopyrrolyl, benzimidazolyl, benzoxazolyl, thionaphthyl, indolyl or purinyl.

The carbocyclic or heterocyclic aryl may have at least one substituent selected from the group consisting of halogens such as chlorine or bromine as in o-chlorophenyl; hydroxyl; lower alkyl such as methyl, ethyl, isopropyl or tert-butyl; alkenyl; alkynyl; trihaloalkyl such as trifluoromethyl; trihaloalkylthio such as trifluoromethyltio; trihaloalkoxy such as trifluoromethoxy; cyano; nitro; amino; substituted amino such as alkylamino, lower monoalkyl amino such as methylamino or ethylamino, lower dialkylamino such as dimethylamino, sulfoamino; lower alkanoyl such as formyl, acetyl; benzoyl; lower alkanoyl amido; lower alkoxy such as methoxy, ethoxy, or isopropoxy; lower alkylthio such as methylthio, ethylthio; free or esterified carboxy such as methoxycarbonyl or ethoxycarbonyl; carbamoyl; substituted carbamoyl; or aryl such as phenyl.

The non-toxic, pharmaceutically acceptable acid addition salts with mineral or organic acids may be the salts formed with the following acids: hydrochloric acid, hydrobromic acid, hydroiodic acid, nitric acid, sulfuric acid, phosphoric acid, propionic acid, acetic acid, formic acid, benzoic acid, maleic acid, fumaric acid, succinic acid, tartric acid, citric acid, oxalic acid, glyoxylic acid, aspartic acid, ascorbic acid alkylmonosulfonic acids such as methanesulfonic acid, ethanesulfonic acid, propanesulfonic acid, alkyldisulfonic acids such as methanedisulfonic acid, α- or β-ethanedisulfonic acid, arylmonosulfonic acids such as benzenesulfonic acid and aryldisulfonic acids.

The carbocyclic such as cycloaklyl, alkyl, alkenyl, alkynyl and alkoxy can be substituted with at least one substituents such as hydroxyl; alkyl, alkenyl or alkynyl as defined above; halogen such as chloro or bromo as in 2-bromo ethyl; alkoxy such as methoxy, ethoxy propoxy or isopropoxy; alkoxyalkyl as in methoxymethyl or 1-ethoxyethyl; aryloxy such as phenoxy; aralkoxy such as benzyloxy; carbocyclic such as cycloalkyl like cyclopropyl, cyclopentyl or cyclohexyl; formyl; acyl like acetyl, propionyl or benzoyl; carboxy; esterified carboxy such as methoxycarbonyl or ethoxy carbonyl; cyano; carbamoyl; substituted carbamoyl like N-(lower monoalkyl) carbamoyl such as N-methylcarbamoyl, N-ethylcarbamoyl, an N,N-(lower dialkyl) carbamoyl such as N,N-dimethylcarbamoyl, N,N-diethylcarbamoyl; N-(lower hydroxyalkyl) carbamoyl such as N-(hydroxymethyl) carbamoyl, N-(hydroxyethyl) carbamoyl, lower carbamoylalkyl such as carbamoylmethyl, carbamoylethyl; aryl includes heterocyclic or carbocyclic optionally substituted such as phenyl or naphthyl; aralkyl like benzyl or phenethyl, diphenylmethyl, triphenylmethyl, thienylmethyl such as 2-thienylmethyl, furylmethyl such as furfurylmethyl, pyridylmethyl or pyrrolylmethyl; mercapto; alkylthio like methylthio or ethylthio; arylthio; aralkylthio; nitro; azido; acyloxy like acetoxy or propionyloxy; phthalimido; acylamido like acetamido or benzamido; amino as in 2-amino-ethyl; substituted amino such as monoalkylamino like methylamino or ethylamino, dialkylamino such as dimethylamino, alkoxycarbonylamino such as methoxycarbonylamino or ethoxycarbonylamino, arylalkoxycarbonylamino such as benzyloxycarbonylamino; amino substituted by a heterocyclic or carbocyclic radical such as anilino.

Among the preferred products of formula I are those wherein the substituent or substituents that can be carried by alkyl, alkenyl, alkynyl and alkoxy are selected from the group consisting of a) hydroxyl,
b) halogens,
c) alkoxy of 1 to 6 carbon atoms,
d) carbocyclic of 3 to 6 carbon atoms optionally substituted by alkyl or alkoxy of 1 to 5 carbon atoms,
e) formyl, acyl of an alkanoic acid of 2 to 6 carbon atoms and benzoyl,
f) free carboxy and esterified by alkyl of 1 to 5 carbon atoms,
g) cyano,
h) carbamoyl optionally substituted by at least one alkyl individually of 1 to 4 carbon atoms,
i) aryl of 6 to 10 carbon atoms optionally substituted,
j) the

in which $R_3$ and $R_4$ individually are hydrogen, alkyl or alkenyl of 1 to 7 carbon atoms optionally substituted by at least one member selected from the group consisting of hydroxyl, alkoxy of 1 to 5 carbon atoms and carboxy free or esterified by alkyl of 1 to 5 carbon atoms, formyl, acyl of an alkanoic acid of 2 to 6 carbon atoms, benzoyl, or an optionally substituted heterocyclic or carbocyclic of 3 to 8 carbon atoms, or $R_3$ and $R_4$ form together with the nitrogen atom to which they are linked a saturated or unsaturated heterocycle of 5 or 6 links optionally containing another heteroatom such as oxygen, nitrogen or sulfur, this heterocycle optionally substituted on the second nitrogen atom in all possible racemic or optically active isomer forms, as well as the addition salts with mineral or organic acids of said products of formula I.

The optional substituent of alkyl, alkenyl, alkynyl or alkoxy are selected preferably from the group consisting of hydroxyl; alkyl and alkoxy such as methyl, ethyl, tert-butyl, methoxy, ethoxy, isopropoxy; alkyl substituted by an alkoxy such as methoxy, ethoxy or isopropoxy; substituted amino such as monoalkyl- and dialkylamino, for example methylamino, ethylamino or dimethylamino; free or esterified carboxy like methoxycarbonyl or ethoxycarbonyl, a lower carbamoylalkyl such as carbamoylmethyl, carbamoylethyl.

The amino —$N(R_3)(R_4)$ can have the same values indicated above for the amino radical —$N(R_1)(R_2)$. The heterocyclic or carbocyclic which can be represented by on the one hand $R_1$ and $R_2$, identical or different, and on the other hand $R_3$ and $R_4$, identical or different, is preferably saturated.

When $R_1$ and $R_2$, on the one hand, or $R_3$ and $R_4$, on the other hand, form, respectively, together with the nitrogen atom to which they are linked, a heterocycle, it may be pyrrolidino, piperidino, morpholino, piperazinyl, methylpiperazinyl, ethylpiperazinyl, propylpiperazinyl, phenylpiperazinyl or benzylpiperazinyl.

The second nitrogen atom which can be contained by the heterocycle formed by $R_1$ and $R_2$ or $R_3$ and $R_4$ can be substituted, for example by alkyl or alkoxy of 1 to 5 carbon atoms such as defined above, phenyl or benzyl optionally substituted by the substituents already mentioned above for the aryl and arylalkyl. There can be mentioned for example, methylpiperazinyl, ethylpiperazinyl, propylpiperazinyl, phenyl piperazinyl or benzylpiperazinyl.

The aryl, aralkyl, aralkenyl or aralkynyl of $X_1$, $X_2$ and $X_3$ cannot be substituted or carry at least one or more substituents chosen for example from the group consisting of hydroxyl; halogen; alkyl like methyl, ethyl, isopropyl or tert-butyl; alkenyl or alkynyl as defined previously; alkoxy such as methoxy, ethoxy or isopropoxy; alkylthio such as methylthio or ethylthio; nitro; amino; substituted amino such as monoalkyl- and dialkylamino like methylamino, ethylamino or dimethylamino; as well as the radicals defined previously for the optional substituents of the alkyl, alkenyl, alkynyl and alkoxy.

Another preferred group of products of formula I are those wherein the substituents which are carried by aryl, aralkyl, aralkenyl, aralkynyl and heterocyclic are selected from the group consisting of halogen, alkyl, alkenyl, alkynyl or alkoxy of 1 to 7 carbon atoms optionally substituted by at least one member selected from the group consisting of hydroxyl, alkoxy of 1 to 5 carbon atoms and carboxy free or esterified by alkyl of 1 to 5 carbon atoms, hydroxyl, trifluoromethyl, trifluoromethylthio, trifluoromethoxy, cyano, nitro, sulfamoyl, amino, monoalkyl- and dialkylamino, formyl, acyl of 2 to 6 carbon atoms and benzoyl, carboxyl free or esterified by alkyl of 1 to 5 carbon atoms, carbamoyl optionally substituted by at least one member selected from the group consisting of alkyl of 1 to 4 carbon atoms, and phenyl optionally substituted by at least one member of the group consisting of halogen, hydroxy, cyano, nitro, alkyl, alkenyl, alkynyl and alkoxy of 1 to 5 carbon atoms, the said products of formula I being in all possible racemic, enantiomer and diastereosomer isomer forms, as well as the addition salts with mineral and organic acids.

In the aralkyl, aralkenyl and aralkyl represented by $X_1$, $X_2$ and $X_3$, the alkyl, alkenyl and alkynyl carried by the aryl are as defined above.

The aryl or substituted aryl represented by $X_1$, $X_2$ or $X_3$ is preferably phenyl, benzyl or phenethyl optionally substituted by at least one member of the group consisting preferably of halogen, hydroxy, cyano, nitro, alkyl, alkenyl, alkynyl and alkloxy of 1 to 5 carbon atoms as defined above and preferably methyl, ethyl, isopropyl and tert-butyl, methoxy, ethoxy and propoxy.

Another preferred group of the products of formula I are those wherein $X_1$, $X_2$ and $X_3$ are selected from the group consisting of hydrogen, alkyl, alkenyl or hydroxyalkyl up to 8 carbon atoms, cyano, formyl or acyl of 2 to 4 carbon atoms, alkoxycarbonyl of 2 to 4 carbon atoms, carbamoyl, amino, dialkylmino wherein the alkyl have 1 to 4 carbon atoms or acylamino of 2 to 4 carbon atoms, phenyl with the proviso that $X_1$, $X_2$ and $X_3$ are not simultaneously selected from the group of hydrogen, alkyl of 1 to 5 carbon atoms, amino and dialkylmino wherein the alkyl contains 1 to 5 carbon atoms, said products being in all possible racemic, enantiomer and diastereoisomer isomer forms, as well as the addition salts with mineral and organic acids of said products of formula I. Preferably, two of the substituents $X_1$, $X_2$, $X_3$ are hydrogen and most preferably in which the sole substituent is situated in position 9 or 11 of the phenyl.

Among the specific products of the invention are [16α(±)]-11-ethenyl-20,21-dinoreburnamenine maleate, [16α(±)]-11-acetyl-20,21-dinoreburnamenine maleate, [16α(±)]-α-methyl-20,21-dinoreburnamenine-11-ethanol fumarate and [16α(±)]-20,21-dinoreburnamenine-11-carboxamide.

The process of the invention for the preparation of the products of formula I comprises reacting a product of the formula

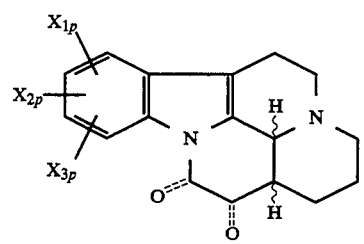

II in which ==O indicates that the single oxo function can be found in position 14 or 15, and $X_{1p}$, $X_{2p}$ and $X_{3p}$ are $X_1$, $X_2$ and $X_3$ as defined above in which the reactive functions are optionally protected with a reducing agent followed by a dehydration and optionally an elimination of the protective groups of the reactive functions which can carry $X_{1p}$, $X_{2p}$ and $X_{3p}$ to obtain the compounds of the formula I and optionally treating the latter with a mineral or organic acid, said products of formula I being in all possible racemic or enantiomer isomer forms.

In a variation of the process for the preparation or products of formula I' which correspond to the products of formula I as defined above in which two of $X_1$, $X_2$ and $X_3$ are hydrogen, comprises either reacting a product of the formula

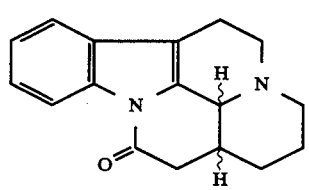

II' with a) either a halogenation reagent to obtain a product of the formula

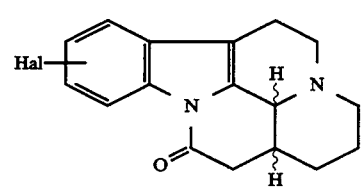

III in which Hal is halogen and subjecting the latter in any order to the following reactions: a reduction reaction of the oxo function followed by dehydration, a substitution reaction of the halogen to obtain the products of the formula

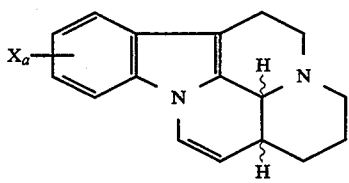

in which $X_a$ has the above meaning for any one of $X_1$, $X_2$ and $X_3$ with the exception of

as defined above, and hydrogen, halogen, alkyl, alkoxy of 1 to 5 carbon atoms, hydroxy, trifluoromethyl and nitro, which products of formula $I'_a$ when $X_a$ is formyl are optionally subjected, to any one of the conversion reactions of the formyl into carbamoyl, hydroxymethyl, cyano or free or esterified carboxyl, b) or to a nitration reaction to obtain a product of the formula

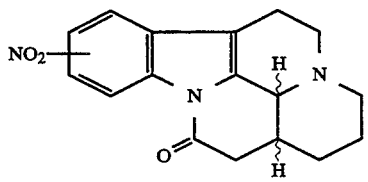

which is subjected to a reduction reaction of the nitro into the amino to obtain a product of the formula

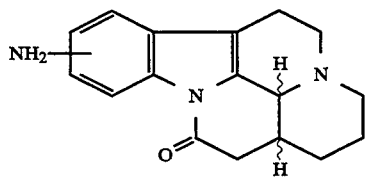

which is subjected to any one of the following reactions 1)- substitution of the amine by halogen via the corresponding diazonium salt to obtain a product of formula III as defined above, 2)- the action of a compound of the formula

in which W is halogen or cyano and $R_1'$ has the above meaning for $R_1$ or $R_2$, with the exception of the heterocycle which can be formed by $R_1$ and $R_2$ with the nitrogen to which they are linked and hydrogen, alkyl of 1 to 5 carbon atoms and acyl of 1 to 6 carbon atoms and in which the reactive function are optionally protected to obtain a product of the formula

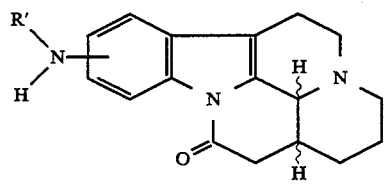

in which $R_1'$ has the above meaning, optionally subjecting the latter to a compound of the formula

in which W is halogen or cyano and $R_2'$ have the above definition to give a product of the formula

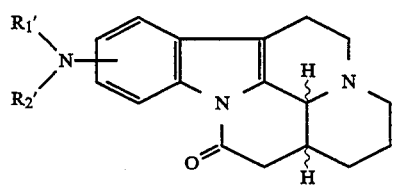

in which $R_1'$ and $R_2'$ have the above meanings and in which the reactive functions are optionally protected, 3)- the action of a compound of the formula

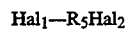

in which $Hal_1$ and $Hal_2$ are individually halogen and $R_5$ is alkyl or alkenyl optionally interrupted by one or more heteroatoms such as oxygen, nitrogen or sulfur and optionally substituted on the nitrogen atom, to obtain a product of the formula

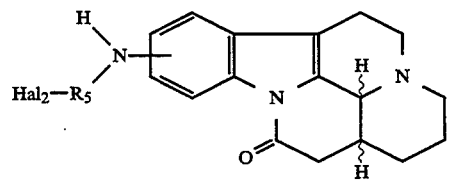

which is subjected to a cyclization reaction to obtain a product of the formula

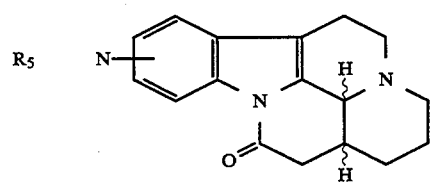

in which

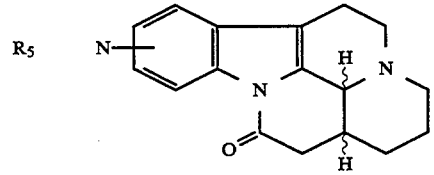

has the meaning above for $R_1$ and $R_2$ when $R_1$ and $R_2$ form a ring with the nitrogen atom to which they are attached and then the products of formulae VII, VII' and VII''' which together are compounds of the formula

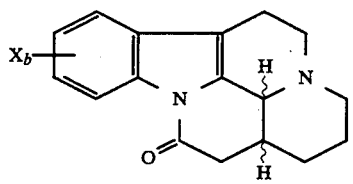

VIII in which $X_b$ has the above meaning for

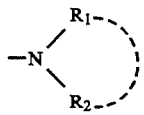

with the exception o the values amino, alkylamino, dialkylamino with alkyl of 1 to 5 carbon atoms and acylamino of up to 6 carbon atoms and in which the reactive functions are optionally protected, are subjected to a reduction followed by dehydration to obtain, after elimination, if necessary and if desired, of the optional protective groups of the reactive functions, a product of the formula

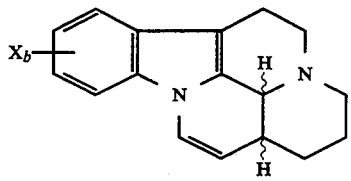

I'b in which $X_b$ has the above meaning or a product of the formula

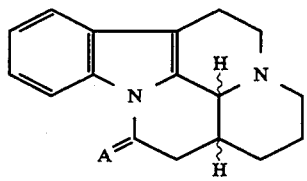

II'' in which A is either an oxo or

is subjected to the action of a compound of the formula $X_c$—Hal     IX in which Hal is halogen and $X_c$ is alkyl of 6 to 18 carbon atoms, alkenyl or acyl as defined above for any one of $X_1$, $X_2$ and $X_3$ in which the reactive functions are optionally protected to obtain a product of the formula

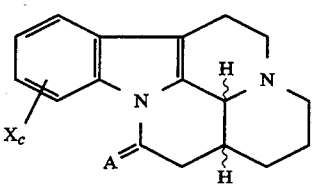

X in which $X_c$ and A have the above meaning and subjecting the latter to a reduction reaction followed by dehydration when --A is oxo or only to a dehydration when A is

to obtain, after elimination, if necessary and if desired, of the optional protective groups of the reactive functions a product of the formula

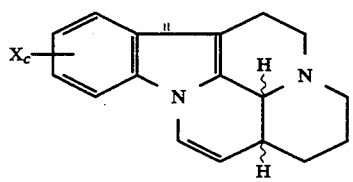

I'c in which $X_c$ has the above meaning and if desired, the products of formulae I'$_a$, I'$_b$, and I'$_c$ are reacted with a mineral or organic acid, said products of formulae I'$_a$, I'$_b$ and I'$_c$ being in all possible racemic or enantiomer isomer forms.

In the preferred conditions for the process of the invention, the reduction reaction followed by dehydration of the compounds of formula II as defined above can be carried out by known so that methods so that the reduction reaction of the ketone function into the alcohol can be carried out with sodium borohydride or sodium cyanoborohydride in the optional presence of lithium chloride in a solvent such as methanol or ethanol. The dehydration reaction of the reduced compound can be carried out either in an acid medium such as hydrochloric acid or p-toluene sulfonic acid or in the presence of copper trifluoroacetate in solvents such as benzene, toluene, xylene.

The halogenation reaction of the product of formula II' is carried out by standard reactions such as by a mineral acid, preferably hydrobromic acid, in the presence of hydrogen peroxide at approximately 60° C. to obtain a product of formula III, the halogen being preferably in the 9- or 11-position. If a mixture of products of formula III is obtained in which the halogen is in the 9 or 11-position, these products can be separated by standard methods such as chromatography. The halogenated products of formula III can be subjected in an any order to the reduction-dehydration reaction and to the substitution reaction of the halogen atom.

When the products of formula III are subjected first to a reduction of the oxo, then to a dehydration, these reactions are carried out as indicated above for the product of formula II. The dehydrated products are then subjected to a substitution of the halogen by $X_a$ which reactin can be carried out using an organo-magnesium compound of the formula $X_a$-Mg-Hal or an organolithium compound of the formula $X_1$-Li prepared by standard conditions known to one skilled in the art.

The halogen of the magnesium halide can be bromine such as phenyl magnesium bromide or allyl magnesium bromide but also iodine or chlorine. The preparation of the magnesium halide can be carried out by reaction of magnesium with an organic halide in a slightly polar inert medium such as ether by the known preparation of organo magnesium halides or Grignard reagents.

The reaction of the dehydrated product with the magnesium halide is preferably carried out in an organic solvent such as tetrahydrofuran or ether for a time from about two hours when $X_a$ is allyl to approximately 10 hours when $X_a$ is phenyl. The reaction is advantageously carried out in the presence of a catalyst such as palladium or nickel.

The preparation of the organo lithium compound can be carried out by the intermediate of a strong base such as diisopropyl-lithium amide or preferably n-butyl-lithium in ethyl ether or tetrahydrofuran at a low temperature of $-70°$ C. to $-10°$ C. The substitution reaction can be carried out by action of a halide, a carbonate or an amide derivative of $X_a$.

When the products of formula III are first subjected to a substitution reaction of the halogen by alkenyl using a corresponding derivative of tin such as

in which $X_a'$ is alkenyl as defined above and $R_6$ is alkyl of 1 to 5 carbon atoms such as vinyl tributyl tin. The reaction is preferably carried out in an organic solvent such as toluene in the presence of a catalyst such as palladium with stirring at reflux. The substituted products may be subjected to a reduction reaction of the oxo, then to a dehydration by standard methods as indicated above for the product of formula II.

The products of formula I'$_a$ may be subjected, if desired, to standard reactions such as oxidation, reduction or substitution of $X_a$. Thus, especially, the formyl of $X_a$ can be converted into hydroxy-methyl, cyano, carbamoyl or free or esterified carboxyl by the usual methods.

The nitration reaction of the product of formula II' to obtain the corresponding products of formula IV can be carried out by a (1/1) mixture of fuming nitric acid and glacial acetic acid. The reduction reaction of the nitro into the amino to obtain the products of formula V can be carried out by catalytic hydrogenation in the presence of platinum in an organic solvent such as a (1/1) mixture of ethanol and ethyl acetate.

The substitution reaction of the amino of the product of formula V by halogen, preferably bromine can be carried out by standard reactions such as the Sandmeyer reaction via the corresponding diazonium salts. The products of formula III obtained can be subjectd to the reactions indicated above to obtain the corresponding products of formua I'$_a$.

The substitution reaction on the primary amine of the product of formula V to obtain the products of formula VII and VII' can be carried out under various known conditions, either by halogen derivatives, the reaction being carried out in the presence of a base such as triethylamine or diethylisopropylamine in a solvent such as toluene or tetrahydrofuran or by cyano derivatives such as aceto nitrile in the presence of sodium cyanoborohydride in a solvent such as formaldehyde. In the case where an acetyl is substituted on the primary amine, the reaction can be carried out using acetyl halide.

The substitution reaction carried out using the appropriate acylated derivative can then be followed, optionally and if desired, by a reduction reaction and the formyl is then reduced to methyl.

Among the compounds of formula VI'' which can be reacted with the products of formula V are dibromo-1,5-pentane, dibromobutane or ethyl dibromo-ether, which results in respectively, after cyclization, a product of formula VIII''' substituted by piperidine, pyrrolidine or morpholine. The reduction reactions of the oxo and the dehydration undertaken on the products of formula VIII can be carried out by standard methods by operating as indicated above.

The reaction of the product of formula II'' with a halogen derivative of formula IX can be carried out by standard methods in the presence of a Lewis acid such as aluminium chloride or in a solvent such as dithiocarbonic anhydride or in solution in the reagent. The products of formula X are then subjected to a reduction reaction followed by dehydration of the oxo or only to a dehydration to obtain the products of formula I'$_c$, these reactions being able to carried out under the conditions indicated above.

The various reactive functions which can be carried by some compounds defined above can, if necessary, be protected which are for example hydroxyl, acyl, free carboxy or also amino and monoalkylamino which can be protected by the appropriate protective groups.

The following non-exhaustive list of examples of protection of the reactive functions can be mentioned: the hydroxy can be protected by trimethylsilyl, dihydropyranyl or methoxy-methyl, the amino can be protected by trityl, benzyl, tert-butyloxycarbonyl, phthalimide or other groups known in the chemistry of the peptides, the acyl such as formyl can be protected in the form of cyclic or non cyclic ketals such as dimethyl or diethyl-ketal or ethylene dioxy ketal, the carboxy groups can be protected in the form of esters formed with easily cleavable esters such as benzylic or tert-butylic esters or esters known in the chemistry of the peptides.

The elimination of these protective groups is carried out under the usual known conditions such as acid hydrolysis with an acid such as hydrochloric acid, benzene sulfonic or p-toluene sulfonic acid, formic acid or trifluoroacetic acid. The phthalimino is eliminatd by hydrazine. A list of various usable protective groups is found in French Patent No. 2,499,995.

The optically active forms of the products of formula can be prepared by resolution of the racemate according to usual methods.

The anti-anoxic compositions are comprised of an anti-anoxically effective amount of at least one compound of formula I and their non-toxic, pharmaceutically acceptable acid addition salts and an inert pharmaceutical carrier or excipient. The compositions may be in the form of tablets, dragees, capsules, granules, suppositories, injectable solutions or suspensions, ointments, creams, gels and aerosols.

Examples of suitable excipients are talc, gum arabic, lactose, starch, magnesium stearate, cocoa butter, aqueous or non-aqueous vehicles, fatty substances of animal or vegetable origin, paraffin derivatives, glycols, various wetting dispersing or emulsifying agents and preservatives.

The compositions have an affinity for the 2 adrenergic receptors and also show useful anti-amnesic properties activating the cognitive functions and show neuronal protective, anti-depressive, anti-anoxic, anti-ischemic properties. They are useful in the treatment of cerebral insufficiencies of anoxic or ischemic origin and in disorders of the memory and attention. They can also be used as anti-depressants.

The novel method of the invention for inducing antianoxic activity in warm-blooded animals, including humans, comprises administering to warm-blooded animals an anti-anoxically effective amount of at least one compound of formula I and its non-toxic, pharmaceutically acceptable acid addition salts. The compounds may be administered orally, rectally, parenterally or topically to the skin and mucous membranes and the usual daily dose is 0.33 to 1 mg/kg depending on the condition treated, the method of administration and the specific compound.

The products of formula $II_A$ corresponding to the products of formula II in which==O is in the 14-position can be prepared as in U.S. Pat. No. 3,838,023 starting with the substituted derivatives of 2, 3, 4, 6, 7, 12-hexahydro-indole (2,3-a) quinolizine. The products of formula $II_B$ corresponding to the products of formula II in which ==O is in the 15-position can be prepared as in U.S. patent application No. 597897 filed on Oct. 15, 1990 now abandoned and refiled as U.S. patent application No. 08/228,300 filed on Apr. 15, 1994. The compounds of formula $II_B$ in which $X_1$, $X_2$ and $X_3$ are hydrogen are described in U.S. Pat. No. 4,316,028.

The starting compounds of the formula

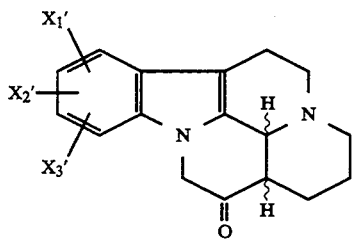

$II_B'$ in which $X_1'$, $X_2'$ and $X_3'$ are individually $X_1$, $X_2$ and $X_3$ with the proviso that at least one of $X_1'$, $X_2'$ and $X_3'$ is not hydrogen can be prepared by the process described in the above patent starting with the corresponding substituted tryptamines.

Another preparation process for the products of formula $II'_B$ consists of subjecting a product of the formula

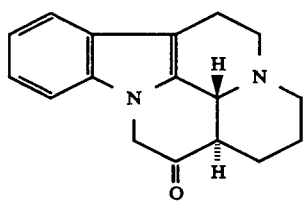

II'a to a nitration reaction to obtain a product of the formula

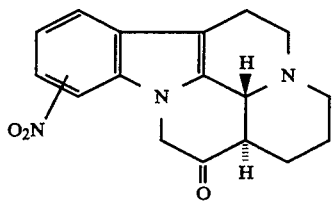

II'b which may be reduced to obtain a product of the formula

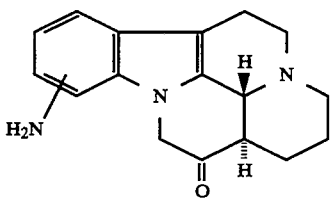

II'c which optionally is either subjected to an alkylation or acylation reaction, or is converted into a diazonium salt from which the compounds of the formula are prepared by known processes:

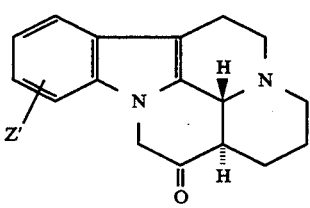

II'd in which Z' is halogen or optionally substituted hydroxy or phenyl, which is optionally converted into the corresponding derivatives in which Z is alkoxy or alkyl.

Certain products of formula $II_B$ are new, namely the compounds of the formula

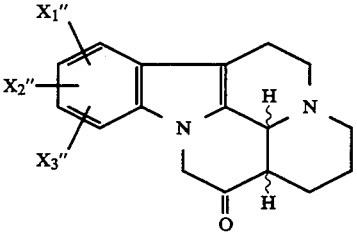

$II''_B$ in which $X_1''$, $X_2''$ and $X_3''$ individually are $X_1$, $X_2$ and $X_3$ with the exception of the products in which $X_1''$, $X_2''$ and $X_3''$ individually are selected from the group consisting of alkyl, alkenyl or alkynyl containing at most 18 carbon atoms and optionally substituted, an optionally substituted alkoxy of 1 to 7 carbon atoms, an amino, mono- or dialkylamino, the alkyls containing 1 to 5 carbon atoms, or an optionally substituted phenyl.

The products of formula II' and II'' are known products and can be prepared as indicated in U.S. Pat. No. 4,316,028 and U.S. Pat. Nos. 3,937,709 and 4,291,038.

Also novel intermediates are the compounds of formulae VIII and X.

In the following examples, there are described several preferred embodiments to illustrate the invention. However, it should be understood that the invention is not intended to be limited to the specific embodiments.

EXAMPLE 1

[16 α(±)]-11-ethenyl-20,21-dinoreburnamenine maleate

Step A: [16 α(±)]-11-ethenyl-20,21-dinoreburnamenin-14 (15H)-one 2.9 ml of vinyl tributyl tin followed by 100 mg of tetrakis (triphenyl phosphone) palladium were added to a solution of 3 g of [16α(±)]-11-bromo-20,21-dinoreburnamenin-14(15H)-one (obtained as in the Belgian Patent No. 44087 B) and 300 ml of toluene and the mixture was stirred for 24 hours at reflux. The insolubles were filtered off and the filtrate was evaporated to dryness under reduced pressure. The residue was chromatographed on silica (eluant: pure ethyl acetate) to obtain 2.1 g of the expected product melting at 164° C.

| IR Spectrum ($CHCl_3$): | |
|---|---|
| C=O | 1704 cm$^{-1}$ |
|  | 1651 cm$^{-1}$ |
| C=C | 1628 cm$^{-1}$ |
| + | 1612 cm$^{-1}$ |
| aromatic | 1565 cm$^{-1}$ |
|  | 1478 cm$^{-1}$ |

Step B: [16 α(±)]-14,15-dihydro-11-ethenyl-20,21-dinoreburnamenin-14-ol 325 mg of sodium borohydride and the 288 mg of lithium chloride were added to a solution of 1 g of the product of Step A in 50 ml of methanol and the mixture was stirred for 6 hours at reflux, cooled and then 100 ml of ice-cooled water were added. The mixture was stirred for 30 minutes, followed by separating and washing with water to obtain 800 mg of the expected product melting at 195° C.

| IR Spectrum ($CHCl_3$): little or no C=O | |
|---|---|
| —OH | 3584 cm$^{-1}$ |
| C=C | 1627 cm$^{-1}$ |
| + | 1602 cm$^{-1}$ |
| aromatic | 1552 cm$^{-1}$ |

Step C: [16α(±)]-11-ethenyl-20,21-dinoreburnamenine maleate 16 mg of p-toluene sulfonic acid were added to a solution of 780 mg of the product of Step B in 50 ml of hot toluene and the mixture was stirred for 15 hours at reflux, cooled and filtered. The filtrate was evaporated to dryness under reduced pressure and the residue was chromatographed on silica (eluant: ethyl acetate) to obtain 480 mg of the desired product melting at 136° C.

457 mg of the base were dissolved in 50 ml of hot ethyl acetate and then a solution of 192 mg of maleic acid in 30 ml of boiling ethyl acetate were added. The mixture was stirred for 3 hours while allowing it to return to ambient temperature, separated, washed and dried at 50° C. under reduced pressure to obtain 600 mg of the desired salt melting at 210° C.

| IR Spectrum ($CHCl_3$): (on the base) | |
|---|---|
| —C=C— | 1649 cm$^{-1}$ |
| C=CH$_2$ | 1627 cm$^{-1}$ |
| aromatic | 1613 cm$^{-1}$ |
|  | 1554 cm$^{-1}$ |
|  | 1477 cm$^{-1}$ |

| Analysis: $C_{23}H_{24}N_2O_4$ | | | |
|---|---|---|---|
| Calculated: | % C 70.39 | % H 6.16 | % N 7.14 |
| Found: | 70.1 | 6.0 | 7.0 |

EXAMPLE 2

[16α(±)]-11-phenyl-20,21-dinoreburnamenine acid maleate 60 mg of nickel diphenyl phosphino propane chloride were added to a solution of 580 mg of [16α(±)]-11-bromo-20,21-dinoreburnamenine (prepared according to BF 2,623,501) in 15 ml of tetrahydrofuran and after the mixture was heated to 50° C., 4.4 ml of a 0.8M solution of phenyl magnesium bromide in tetrahydrofuran were added. The medium was held under these conditions for 5 hours and then was poured into 50 ml of ice-cooled water and extracted with ethyl acetate. The extracts were washed with water, dried and brought to dryness under reduced pressure. The residue was chromatographed on silica (eluant: methylene chloride—acetonitrile (8-2)) to obtain 510 mg of the expected product melting at 145° C.

200 mg of maleic acid in solution in 10 ml of boiling ethyl acetate were added to a solution of 560 mg of above base in 40 ml of ethyl acetate and 10 ml of ethanol. The mixture was stirred for 5 hours at ambient temperature and after separating and drying at 70° C. under reduced pressure, 585 mg of the expected salt were obtained melting at 230° C.

| IR Spectrum ($CHCl_3$): | |
|---|---|
|  | 1650 cm$^{-1}$ |
| C=C | 1612 cm$^{-1}$ |
| + | 1600 cm$^{-1}$ |
| aromatic | 1555 cm$^{-1}$ |
|  | 1499 cm$^{-1}$ |

| Analysis: $C_{27}H_{26}N_2O_4$; molecular weight = 442.52 | | | |
|---|---|---|---|
| Calculated: | % C 73.28 | % H 5.92 | % N 6.33 |
| Found: | 73.0 | 5.7 | 6.4 |

EXAMPLE 3

[16α(±)]-11-(2-propenyl)-20,21-dinoreburnamenine acid maleate

Using the procedure of Example 2, 1 g of [16α(±)-11-bromo-20,21-dinoreburnamenine (prepared in BF 2,623,501) and 4 ml of a 1M solution of allyl magnesium bromide in tetrahydrofuran were reacted to obtain after chromatography on silica (eluant: methylene chloride—acetonitrile (8-2)) 450 mg of the desired product melting at ≦70° C. in the form of the base.

430 mg of the base were salified using the procedure of Example 2 to obtain 525 mg of the expected maleate melting at 170° C.

| IR Spectrum (CHCl$_3$): | |
|---|---|
| —C=C— + aromatic =CH$_2$ | 1651 cm$^{-1}$ 1612 cm$^{-1}$ 1560 cm$^{-1}$ 1636 cm$^{-1}$ 919 cm$^{-1}$ |

Bohlmann bands.

| Analysis: C$_{24}$H$_{26}$N$_2$O$_4$; molecular weight = 406.486 | | | |
|---|---|---|---|
| Calculated: | % C 70.92 | % H 6.45 | % N 6.89 |
| Found | 70.8 | 6.4 | 6.8 |

EXAMPLE 4

[16α(±)]-11-acetyl-20,21-dinoreburnamenine acid maleate 8 g of aluminium chloride were added at 0° C. to a suspension of 4.03 g of [16α(±)]-20,21-dinoreburnamenine-14(15H)-one (prepared in BF 2,381,048) and 100 ml of acetyl chloride and after the mixture was stirred for one hour at ambient temperature, it was poured into ice-cooled water. The mixture was alkalized by adding concentrated liquid ammonia and was extracted with ethyl acetate. The extracts were washed with water, dried and evaporated to dryness under reduced pressure. The residue was taken up in 200 ml of toluene and 200 mg of p-toluene sulfonic acid were added. The medium was heated at reflux for 15 hours and the insoluble part was filtered off. The filtrate was evaporated to dryness under reduced pressure and the residue was chromatographed on silica (eluant: ethyl acetate—isopropyl ether (8-2)) to obtain 1.47 g of the desired product melting at 144° C. in the form of the base. A solution of 294 mg of maleic acid in 20 ml of ethanol was added to a solution of 750 mg of the base in a mixture of 50 ml of ethyl acetate and 50 ml of ethanol. The mixture was stirred for a few minutes, followed by separating and drying under reduced pressure at 80° C. to obtain 820 mg of the expected product melting at 246° C.

| IR Spectrum (CHCl$_3$): | |
|---|---|
| >=O | 1667 cm$^{-1}$ |
| —C=C— + aromatic | 1646 cm$^{-1}$ 1613 cm$^{-1}$ 1600 cm$^{-1}$ 1554 cm$^{-1}$ |

| Analysis: C$_{23}$H$_{24}$N$_2$O$_5$; molecular weight = 408.457 | | | |
|---|---|---|---|
| Calculated: | % C 67.64 | % H 5.92 | % N 6.86 |
| Found: | 67.5 | 5.9 | 6.8 |

EXAMPLE 5

[16α(±)]-α-methyl-20,21-dinoreburnamenine-11-ethanol acid fumarate 850 mg of sodium borohydride were added slowly to a suspension of 1.3 g of [16α(±)]-(20,21-dinoreburnamenin-11-yl) ethanone of Example 4 with 30 ml of methanol. The mixture was stirred for 2 hours at ambient temperature and 100 ml of ice-cooled water were added. Separation was carried out, followed by washing with water and drying at 85° C. under reduced pressure. After purification by impasting in acetone, 1.01 g of the desired product melting at 214° C. in the form of the base were obtained. 1 g of the base was dissolved in a mixture of 50 ml of ethanol and 100 ml of ethyl acetate and a solution of 394 mg of fumaric acid in 20 ml of boiling ethanol was added. After stirring for 2 hours at 0° C., and separating, 930 mg of the expected product melting at 225° C. were obtained.

| IR Spectrum: | |
|---|---|
| C=C + aromatic | 1649 cm$^{-1}$ 1612 cm$^{-1}$ 1560 cm$^{-1}$ |

| Analysis: C$_{23}$H$_{26}$N$_2$O$_5$; molecular weight = 410.473 | | | |
|---|---|---|---|
| Calculated: | % C 67.3 | % H 6.38 | % N 6.82 |
| Found: | 67.3 | 6.4 | 6.7 |

EXAMPLE 6

[16α(±)]-20,21-dinoreburnamenin-11-carboxaldehyde acid maleate 7.3 ml of a 1.6M solution of n-butyl lithium in hexane were added to a solution cooled down to —70° C. of 3 g of [16α (±)]-11-bromo-20,21-dinoreburnamenine (prepared by BF 2,623,501) in 50 ml of tetrahydrofuran. The mixture was stirred for 45 minutes at —70° C. and 1.4 ml of dimethylformamide in solution in 3 ml of tetrahydrofuran were added at —70° C. The mixture was allowed to return to 0° C. and was stirred for 40 minutes at 0° C. and poured into an aqueous solution of ammonium chloride. The mixture was extracted with ethyl acetate and the extracts were dried and evaporated to dryness under reduced pressure. The residue was chromatographed on silica (eluant: ethyl acetate) to obtain 2.11 g of the expected product in the form of the base melting at 132° C.

1 g of the base was dissolved in a mixture of 40 ml of ethanol and 60 ml of ethyl acetate and a solution of 147 mg of maleic acid in 20 ml of ethanol was added. The mixture was stirred for 2 hours at 20° C., separated, washed with ethanol, and dried at 70° C. under reduced pressure to obtain 1.06 g of the desired product melting at 225° C.

| IR Spectrum: | |
|---|---|
| =O | 1682 cm$^{-1}$ |
| —C=C— + aromatic | 1644 cm$^{-1}$ 1613 cm$^{-1}$ 1596 cm$^{-1}$ 1558 cm$^{-1}$ |

| Analysis: C$_{22}$H$_{22}$N$_2$O$_5$; molecular weight = 394.43 | | | |
|---|---|---|---|
| Calculated: | % C 67 | % H 5.62 | % N 7.1 |
| Found | 67 | 5.6 | 7.1 |

EXAMPLE 7

[16α(±)]-20,21-dinoreburnamenine-11-methanol acid fumarate 341 mg of sodium borohydride were added slowly at 20° C. to a solution of 1.1 g of [16α(±)]-20,21-dinoreburnamenine-11-carboxaldehyde in the form of the base of Example 6 in 50 ml of methanol, and the mixture was stirred for 2 hours. 200 ml of water were added followed by separating, washing with water, then with acetone to obtain 967 mg of the expected product in the form of base melting at 214° C.

400 mg of fumaric acid in solution in 20 ml of boiling ethanol were added to a solution of 967 mg of the base in 120 ml of an ethyl acetate—ethanol mixture (1-1). After separating, 1.1 g of the expected product melting at 255° C. were obtained.

| IR Spectrum: little or no >=O | |
|---|---|
| OH | 3610 cm$^{-1}$ |
| —C=C— + aromatic | { 1649 cm$^{-1}$ <br> 1616 cm$^{-1}$ |

| Analysis: $C_{22}H_{24}N_2O_5$; molecular weight = 396.446 | | | |
|---|---|---|---|
| Calculated: | % C 66.65 | % H 6.1 | % N 7.07 |
| Found: | 67.0 | 6.3 | 6.9 |

EXAMPLE 8

Ethyl [16α(±)]-20,21-dinoreburnamenine-11-carboxylate acid maleate

Using the procedure of Example 6, 3.29 g of [16α-(±)]-11-bromo-20,21-dinoreburnamenine (obtained by BF 2,623,501) and 1.8 ml of ethyl carbonate were reacted to obtain after chromatographing on silica, (eluant: ethyl acetate—isopropyl ether (8-2)), 1.36 g of the expected product in the form of the base melting at 110° C.

216 mg of maleic acid in solution in 10 ml of ethanol were added to a solution of 600 mg of the base in 50 ml of ethyl acetate and 10 ml of ethanol. The mixture was stirred for a few moments, followed by separating and washing with ethyl acetate to obtain 460 mg of the desired product melting at 230° C.

| IR Spectrum | |
|---|---|
| >=O | 1702 cm$^{-1}$ |
| —C=C— + aromatic | { 1646 cm$^{-1}$ <br> 1612 cm$^{-1}$ <br> 1560 cm$^{-1}$ <br> 1477 cm$^{-1}$ |

| Analysis: $C_{24}H_{26}N_2O_6$; molecular weight = 438.48 | | | |
|---|---|---|---|
| Calculated: | % C 65.74 | % H 5.98 | % N 6.39 |
| Found: | 65.9 | 5.9 | 6.5 |

EXAMPLE 9

[16α(±)]-20,21-dinoreburnamenine-11-carbonitrile acid maleate

Gaseous ammonia was added to a solution of 1.4 g of [16α(±)]-20,21-dinoreburnamenine-11-carboxaldehyde (Example 6) in 50 ml of isopropanol by bubbling through until saturation was reached and while maintaining this bubbling, 8.7 g of manganese dioxide were added. The mixture was stirred for 3 hours at ambient temperature and after 20 ml of methylene chloride were added, the reaction medium was filtered. The filtrate was evaporated to dryness under reduced pressure and the residue was chromatographed on silica (eluant: ethyl acetate) to obtain 1.3 g of the desired product in the form of the base melting at 146° C.

295 mg of maleic acid in solution in 10 ml of ethanol were added to a solution of 700 mg of the base in 40 ml of ethyl acetate and 10 ml of ethanol. The mixture was stirred for 2 hours at ambient temperature and separated to obtain 830 mg of the expected product melting at 228° C.

| IR Spectrum (CHCl$_3$): | |
|---|---|
| —C≡N <br> Bohlmann bands | 2222 cm$^{-1}$ (F) |
| C=C C=N + aromatic | { 1646 cm$^{-1}$ <br> 1614 cm$^{-1}$ <br> 1605 cm$^{-1}$ <br> 1555 cm$^{-1}$ |

| Analysis: $C_{22}H_{21}N_3O_4$; molecular weight = 321.43 | | | |
|---|---|---|---|
| Calculated: | % C 67.51 | % H 5.41 | % N 10.73 |
| Found: | 67.7 | 5.2 | 10.8 |

EXAMPLE 10

[16α(±)]-20,21-dinoreburnamenine-11-carboxamide 20 ml of 5N sodium hydroxide and then 2 ml of hydrogen peroxide were added to a solution of 600 mg of the product of Example 9 in 30 ml of methanol and the mixture was stirred for 3 hours at ambient temperature. 100 ml of water were added, followed by separating, washing with water and drying at 75° C. under reduced pressure to obtain 580 mg of crude product melting at 258° C. which was impasted in ethanol to recover 410 mg of the desired product melting at 258° C.

| IR Spectrum: | |
|---|---|
| >=O | 1638 cm$^{-1}$ |
| aromatic + <br> NH$_2$ + C=C | { 1610 cm$^{-1}$ <br> 1554 cm$^{-1}$ |

| Analysis: $C_{18}H_{19}N_3O$; molecular weight = 293.37 | | | |
|---|---|---|---|
| Calculated: | % C 73.7 | % H 6.53 | % N 14.32 |
| Found: | 73.4 | 6.3 | 14.2 |

EXAMPLE 11

[16α(±)]-11-octyl-20,21-dinoreburnamenine acid maleate

Using the procedure of Example 6, 2 g of [16α(±)]-11-bromo-20,21-dinoreburnamenine (prepared according to BF 2,623,501) and 2.2 ml of n-octyl iodide were reacted to obtain after chromatography on silica (eluant: methylene chloride—acetonitrile (85-15)), 280 mg of the expected product in the form of the base melting at 156° C.

A solution of 365 mg of maleic acid in 30 ml of ethyl acetate was added to a solution of 1.14 g of the base in 50 ml of ethyl acetate and after separating, 1.19 g of the desired salt were obtained melting at 140° C.

| IR Spectrum: (CHCl₃): | |
|---|---|
| strong aliphatic Bohlmann bands | |
| —C=C— + aromatic | 1651 cm$^{-1}$ 1613 cm$^{-1}$ 1556 cm$^{-1}$ |

| Analysis: $C_{29}H_{38}N_2O_4$; molecular weight = 478.63 | | | |
|---|---|---|---|
| Calculated: | % C 72.77 | % H 8.00 | % N 5.85 |
| Found: | 72.9 | 8.0 | 6.0 |

EXAMPLE 12

Pharmaceutical Composition

Tablets were prepared containing 25 mg of the product of Example 1 and sufficient excipient of lactose, talc, starch and magnesium stearate for a tablet weight of 300 mg.

PHARMACOLOGICAL STUDY

1 Hypobaric Anoxia

The test consisted of measuring the survival time of mice subjected to a lethal hypoxic atmosphere in which male mice of CD1, Charles River type, weighing 20 to 25 grams, were placed individually in a 2 liter enclosure in which a depression of 620 mm Hg was brought about by means of a vacuum pump, according to the following kinetics:

| Time (s) | depression (mmHg) |
|---|---|
| 0 | 0 |
| 3.5 | 350 |
| 6 | 400 |
| 9 | 450 |
| 12 | 500 |
| 16 | 550 |
| 28 | 600 |
| 34 | 610 |
| 55 | 620 |

The survival time was the time between the start of the depression (T0) and the last respiratory movement; it was on the order of 70 to 80 seconds on the control animals. The results are given as a percentage of the increase in the survival time relative to the control animals who received the vehicle.

| Product of Example | % increase of survival time |
|---|---|
| 4 | +22 |
| 5 | +21 |
| 10 | +22 |

2 Affinity for Alpha 2 Adrenergic Receptors 10 cortices removed from the brains of male rate weighing on average 150 g were homogenized in 90 ml of 0.32M sucrose. After centrifuging the homogenized mixture at 1,000 g for 10 minutes at 0° C., the supernatant was centrifuged at 30,000 g for 10 minutes at 0° C.+4° C. The deposit was suspended in 240 ml of 50 mM Tris HCl pH 7.7 buffer and centrifuged at 30,000 g for 15 minutes at 0° C.+4° C. The new deposit was suspended in 480 ml of 50 mM NaKPO₄ pH 7.4 buffer. Then 2 ml of suspension were incubated for 45 minutes at 25° C. in the presence of H³ rauwolscine it a concentration of 0.15 nM:

i) on its own, ii) with increasing concentrations of the product under test or, iii) to determine the non-specific fixation, with non-radioactive phentolamine at a concentration of $10^{-5}$ M.

The incubated suspensions were filtered on Whatman GF/C and the filters were washed three times with 5 ml of NaKPO₄ pH 7.4 buffer at 0° C. The radioactivity of the filters was measured by liquid scintillation. The affinity of the product tested for the alpha 2 adrenergic receptors was determined relative to phentolamine as reference product.

CD = concentration of phentolamine inhibiting 50% of the specific fixation of H³ rauwolscine;

CX = concentration of the product tested inhibiting 50% of the specific fixation of H³ rauwolscine.

The relative affinity was given by the relationship:

$$RBA = 100 \frac{CD}{CX}$$

The product of Example 1 had a RBA equal to 31.

3 Acute Toxicity

The lethal doses LD₀ of the different compounds tested were evaluated after oral administration to a mouse.

The maximum dose which did not cause any mortality in 8 days was called LD₀. The results obtained are as follows:

| Product of Example | % increase of survival time |
|---|---|
| 1 | ≧400 |
| 4 | 100 |
| 5 | 100 |

Various modifications of the compounds and method of the invention may be made without departing from the spirit or scope thereof and it is to be understood that the invention is intended to be limited only as defined in the appended claims.

What we claim is:

1. A compound in all racemic or optionally active forms selected from the group consisting of a compound of the formula

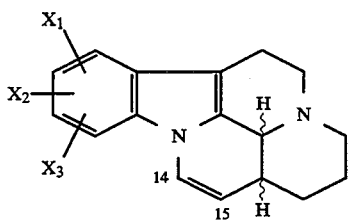

wherein $X_1$ and $X_2$ are hydrogen, $X_3$ is in the 11-position and is selected from the group consisting of ethenyl, phenyl, acetyl, 2-hydroxy ethyl, hydroxyl methyl, ethyl carboxylate, carbonitrile and carboxamide and their non-toxic, pharmaceutically acceptable acid addition salts.

2. A compound of claim 1 selected from the group consisting of [16α(±)]-11-ethenyl-20,21-dinoreburnamenine maleate, and [16α(±)]-11-acetyl-20,21-dinoreburnamenine maleate.

3. A composition for inducing antianoxic activity comprising an antianoxically effective amount of at least one compound of claim 1 and an inert pharmaceutical carrier.

4. A composition of claim 3 wherein the active compound is selected from the group consisting of [16α(±)]-11-ethenyl-20,21-dinoreburnamenine maleate, and [16α(±)]-11-acetyl-20,21-dinoreburnamenine maleate.

5. A method of inducing anti-anoxic activity in warm-blooded animals comprising administering to warm-blooded animals an anti-anoxically effective amount of at least one compound of claim 1.

6. A method of claim 5 wherein the active compound is selected from the group consisting of [16α(±)]-11-ethenyl-20,21-dinoreburnamenine maleate, and [16α(±)]-11-acetyl-20,21-dinoreburnamenine maleate.

7. A compound of the formula

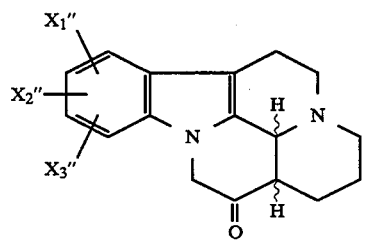

wherein $X_1''$ and $X_2''$ are hydrogen and $X_3''$ is selected from the group consisting of acetyl, ethyl carboxylate, carbonitrile and carboxamide.

* * * * *